United States Patent
Kim et al.

(10) Patent No.: US 7,371,217 B2
(45) Date of Patent: May 13, 2008

(54) DEVICE FOR THE NON-INVASIVE MEASUREMENT OF BLOOD GLUCOSE CONCENTRATION BY MILLIMETER WAVES AND METHOD THEREOF

(75) Inventors: Dong-kyun Kim, Suwon-si (KR); Jong-hwa Won, Suwon-si (KR); Viacheslav Viacheslavovich Meriakri, Moscow (RU); Evgenii Even'evich Chigrai, Moscow (RU)

(73) Assignee: Samsung Electronics Co., Ltd., Suwon (KR)

( * ) Notice: Subject to any disclaimer, the term of this patent is extended or adjusted under 35 U.S.C. 154(b) by 509 days.

(21) Appl. No.: 11/154,558

(22) Filed: Jun. 17, 2005

(65) Prior Publication Data

US 2006/0025664 A1 Feb. 2, 2006

(30) Foreign Application Priority Data

Jun. 17, 2004 (KR) ...................... 10-2004-0045158

(51) Int. Cl.
*A61B 5/00* (2006.01)
(52) U.S. Cl. .................. 600/365; 600/310; 600/309
(58) Field of Classification Search ........ 600/345–366, 600/309, 310, 319, 316
See application file for complete search history.

(56) References Cited

U.S. PATENT DOCUMENTS

| | | | | |
|---|---|---|---|---|
| 5,137,023 A | * | 8/1992 | Mendelson et al. | ......... 600/316 |
| 6,753,520 B2 | * | 6/2004 | Spirin et al. | ........... 250/227.16 |
| 7,271,912 B2 | * | 9/2007 | Sterling et al. | ............. 356/436 |
| 2005/0037384 A1 | * | 2/2005 | Braig et al. | .................... 435/6 |
| 2005/0037482 A1 | * | 2/2005 | Braig et al. | .............. 435/287.1 |

* cited by examiner

*Primary Examiner*—Charles A. Marmor, II
*Assistant Examiner*—Navin Natnithithadha
(74) *Attorney, Agent, or Firm*—Sughrue Mion, PLLC

(57) ABSTRACT

A device and method for the non-invasive measurement of blood glucose concentrations by millimeter waves. The device includes a millimeter wave generator; a TE10 mode rectangular waveguide transmitting a millimeter wave generated by the millimeter wave generator; and a plane parallel plate chosen to yield a minimal point of the power reflection coefficient of the millimeter wave incident to and reflected from the dielectric object under test via the TE10 mode rectangular waveguide and the plane parallel plate. The device also includes power detectors detecting the powers of the incident wave generated by the millimeter wave generator and the reflected wave from the dielectric object via the plane parallel plate; a temperature sensor measuring a temperature of the dielectric object; and a reader reading the minimum power reflection coefficient and a corresponding frequency from the incident and reflected wave detected by the power detectors.

8 Claims, 4 Drawing Sheets

DEVICE FOR THE NON-INVASIVE MEASUREMENT OF BLOOD GLUCOSE CONCENTRATION BY MILLIMETER WAVES AND METHOD THEREOF

CROSS-REFERENCE TO RELATED APPLICATIONS

This application claims priority from Korean Patent Application No. 2004-45158, filed on Jun. 17, 2004, in the Korean Intellectual Property Office, the entire contents of which are incorporated herein by reference.

BACKGROUND OF THE INVENTION

1. Field of the Invention

Methods and apparatuses consistent with the present invention relate to measuring dielectric characteristics of a dielectric having high dielectric loss, and more particularly, to non-invasive measurement of blood glucose concentrations by millimeter waves.

2. Description of the Related Art

Diabetics have suddenly increased in number due to lack of physical activity and changes in eating habits. The deaths caused by diabetes in 2001 in Korea are 23.8 people per hundred thousand people, and diabetes now stands fourth in causes for death in Korea. This rate has more than doubled since 1990. Individual diabetics must measure blood glucose by themselves due to the increase in number, i.e., self-monitoring of blood glucose is required. The self-monitoring of blood glucose is an important component of modern therapy for diabetes mellitus and offers detailed information about blood glucose levels at many times points to enable maintenance of more constant glucose levels in everyday life. As a general rule, most patients with type 1 diabetes are recommended to test their blood glucose level at least three or four times per day. However, it is reported that only 18% of diabetics periodically measure blood glucose, even in the U.S.A. which has a good social welfare. Such negligence of the self-monitoring of blood glucose is due to current invasive-type glucose meters which require blood samples directly taken from the body. Periodical tests by the invasive method not only gives pain or uncomfortable feelings during taking of the blood sample, but also imposes mental and economic burdens with considerable costs of consumable accessories necessary for taking the blood samples.

Devices for the non-invasive measurement of blood glucose have been developed to solve such pain and displeasure during taking blood and smoothly perform self-monitoring of blood glucose. As non-invasive measurement methods of blood glucose, methods of using an analysis of an absorption spectrum in an infrared zone and a method of using impedance spectroscopy in a band of tens to hundreds of MHz have been studied. Some prototypes or products have been researched and developed according to the above-mentioned method. To observe the validity of the non-invasive measurement of blood glucose in a millimeter wave band, dielectric characteristics of a glucose-0.9% NaCl solution depending on a glucose concentration in a band between 30 GHz and 40 GHz are investigated using an open-ended coaxial line method and a transmission coefficient measurement method.

To non-invasively measure the dielectric constant e' and dielectric loss e'' of dielectric materials having a high dielectric loss in a millimeter wave band, the modulus and phase of the reflection coefficient of the reflected electromagnetic wave from the dielectric object are generally measured according to the open-ended coaxial line method using a vector network analyzer. However, it is known that a measurement accuracy of the dielectric constant e' using the vector network analyzer is on a level of ±5%. The main problem with solids is the contact between the coaxial probe and the material under test, which causes inaccuracy and low reproducibility of the measurement. According to the experimental results performed in the frequency band between 30 GHz and 40 GHz, the variations of 0.3 to 0.6 in the dielectric constant $\Delta\epsilon'$ of the glucose-saline solutions having the dielectric constants between 20 and 30 have been reported. However, such a precise measurement is impossible in consideration of the measurement accuracy of the vector network analyzer.

SUMMARY OF THE INVENTION

An aspect of the present invention provides a device and a method for a non-invasive and periodic self-measurement of a blood glucose concentration at a higher accuracy using millimeter waves.

According to an aspect of the present invention, there is provided a device for a non-invasive measurement of blood glucose concentrations by millimeter waves, including: a millimeter wave generator creating electromagnetic waves in a specified frequency band; a TE10 mode rectangular waveguide transmitting a millimeter wave generated by the millimeter wave generator; a plane parallel plate having a refractive index and a thickness chosen to yield a minimal point of the power reflection coefficient of the reflected millimeter wave in the specified frequency band and being installed between an end of the waveguide and the dielectric object under test, such as the skin of human body or blood; power detectors detecting the powers of an incident and a reflected waves incident to or reflected from the dielectric object through the waveguide and the plane parallel plate; a temperature sensor measuring a temperature of the object to compensate for the output variation caused by the temperature change of the object; and a reader reading the minimal point of the power reflection coefficient and a corresponding frequency in the specified frequency band.

The device may further comprise a calculating unit calculating dielectric characteristics of the object and its glucose concentration based on the minimum power reflection coefficient and the corresponding frequency which are read from the reader and the temperature of the object which is obtained by the temperature sensor, a display displaying the resultant calculated by the calculating unit, and a controller controlling the components for the automatic measurement.

As described above, the device for the non-invasive measurement of blood glucose concentrations by millimeter waves is designed to yield the minimal point of the power reflection coefficient of the millimeter wave reflected from the high-loss dielectric object, such as skin or a blood sample, in the specified frequency band. Accordingly, the glucose concentration in the body or blood sample is determined based on the minimum power reflection coefficient and the corresponding frequency which changes according to the glucose concentration.

According to another aspect of the present invention, there is provided a non-invasive measurement method of blood glucose concentrations by millimeter waves, including: installing a plane parallel plate, which is made of a low dielectric loss material and of which refractive index and thickness are chosen to yield a minimal point of the power reflection coefficient in the specified frequency band in which the glucose concentration of the object is to be measured, at an end of a TE10 mode rectangular waveguide transmitting a millimeter wave to be positioned at a front end of a dielectric object under test; detecting the minimum power reflection coefficient and the corresponding frequency of the millimeter wave, reflected from the dielectric object under test via the TE10 mode rectangular waveguide and the plane parallel plate, in the specified frequency band; measuring the temperature of the object using a temperature sensor; and determinating the glucose concentration of the object from information of the measured minimum power reflection coefficient, the corresponding frequency, and the temperature of the object.

BRIEF DESCRIPTION OF THE DRAWINGS

These and other aspects of the present invention will be more apparent by describing certain embodiments of the present invention with reference to the accompanying drawings, in which.

DETAILED DESCRIPTION OF EXEMPLARY EMBODIMENTS OF THE INVENTION

Figure 1:
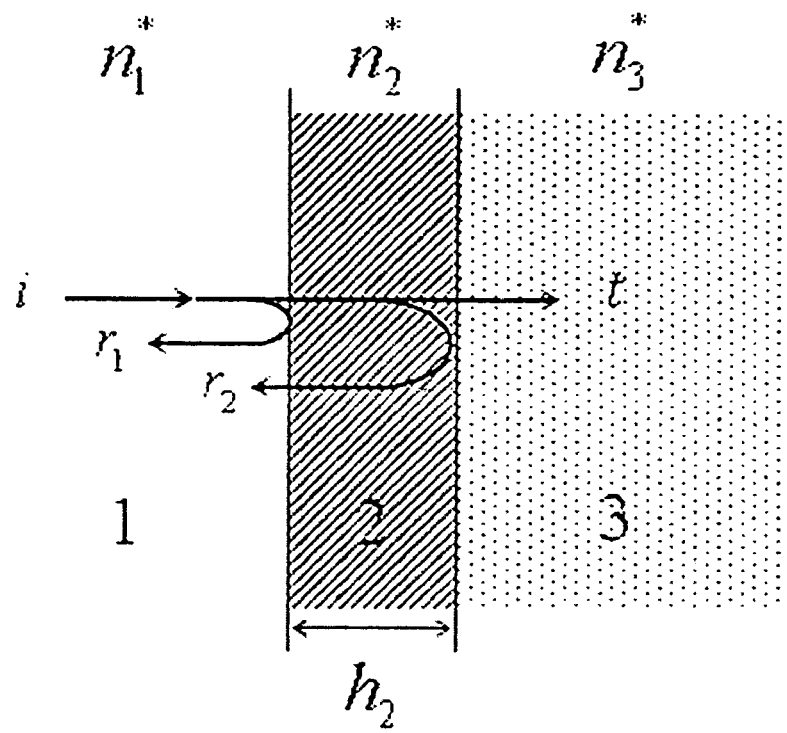
FIG. 1 is a view illustrating three dielectric structures stacked in parallel with one another in a free space to explain a measurement principle of a device for a non-invasive measurement of blood glucose concentrations using millimeter waves according to an exemplary embodiment of the present invention.

Hereinafter, exemplary embodiments according to the present invention will be described in greater detail with reference to the accompanying drawings.

In the following description, same drawing reference numerals are used throughout the drawings for the same elements. The matters defined in the description such as a detailed construction and elements are nothing but the ones provided to assist in a comprehensive understanding of the invention. Thus, it is apparent that the present invention can be carried out without those defined matters. Also, well-known functions or constructions are not described in detail since they would obscure the invention in unnecessary detail.

FIG. 1 is a view illustrating three dielectric structures stacked in parallel with one another in a free space to explain a measurement principle of a device for non-invasive measurement of blood glucose concentrations using millimeter waves according to an exemplary embodiment of the present invention. The dielectric structures are air, a plane parallel plate, and a dielectric object under test having complex refractive indexes $n^*_1$, $n^*_2$, and $n^*_3$ from the left. Here, $n^*_j$ (complex refractive index)$=n_j+ik_j$ ($j=1,2,3$ and $i=\sqrt{-1}$). In a case where a uniform plane wave is incident normally on two-interfaces of media as shown in FIG. 1, the (complex-valued) reflection coefficient $r^*$ at the incident side of the interface between air and the plane parallel plate is calculated as in Equation 1:

$$r^* = \frac{r^*_{12} + r^*_{23}\exp(2i\beta^* h_2)}{1 + r^*_{12}r^*_{23}\exp(2i\beta^* h_2)} \quad (1)$$

wherein $r^*_{12}$ and $r^*_{23}$ denote the elementary reflection coefficients at the incident sides of two interfaces which are expressed with the complex refractive indexes $n^*_1$, $n^*_2$, $n^*_3$ of the dielectric structures as in Equations 2a and 2b:

$$r^*_{12} = |r^*_{12}|e^{\varphi_{12}} = r_{12}e^{\varphi_{12}} = \frac{n^*_1 - n^*_2}{n^*_1 + n^*_2} \quad (2a)$$

$$r^*_{23} = |r^*_{23}|e^{\varphi_{23}} = r_{23}e^{\varphi_{23}} = \frac{n^*_2 - n^*_3}{n^*_2 + n^*_3} \quad (2b)$$

Also, $\beta^*$ in Equation 1 is a propagating wavenumber in the plane parallel plate which is expressed with the complex refractive index $n^*_2$ and a frequency f of the incident plane wave as in Equation 3:

$$\beta^* = \frac{2\pi}{\lambda_0}n^*_2 = \frac{2\pi f}{c}n^*_2 \quad (3)$$

wherein c denotes a speed of light in the free space, and $?_0$ denotes a wavelength of an electromagnetic wave propagated to the frequency f in free space.

It is known that a refractive index of air is 1, and an imaginary part k2 of the complex refractive index of the plane parallel plate made of a low-loss dielectric is sufficiently small and thus may be neglected. Therefore, Equations 2a and 2b can be rewritten as in Equations 4a and 4b:

$$r^*_{12} = r_{12} = \frac{1 - n^*_2}{1 + n^*_2} \quad (4a)$$

$$r^*_{23} = \frac{(n_2 - n_3) - ik_3}{(n_2 + n_3) + ik_3} \quad (4b)$$

If a refractive index (a real part of a complex refractive index) $n_2$ and a thickness $h_2$ of a medium 2, i.e., the plane parallel plate, is given at a frequency $f_m$ of a uniform plane wave as in Equations 5 and 6, a phase difference between an incident wave and a reflected wave is 180° and thus, the complex reflection coefficient in Equation 1 is 0, i.e., an ideal reflectionless condition may be obtained.

$$n_2 = \sqrt{n_3 + \frac{k_3^2}{n_3 - 1}} \qquad (5)$$

$$h_2 = \frac{(2s+1)c}{4n_2 f_m} - \arctan\left(\frac{2n_2 k_3}{n_3^2 + k_3^2 - n_2^2}\right)\frac{c}{4\pi n_2 f_m} \qquad (6)$$

wherein s is an arbitrary integer.

However, in current practice, there is substantially no dielectric substance having the refractive index $n_2$ given in Equation 5, and the plane parallel plate is not easily manufactured to have the thickness $h_2$ determined in Equation 6. Thus, a plane parallel plate satisfying the conditions of Equations 5 and 6 may be difficult to embody. As a result, a power reflection coefficient at the frequency $f_m$ is substantially a minimum value $R_m(=|r^*_m|^2)$. If the conditions in Equations 1, 5, and 6 are applied, a complex refractive index $n_3+ik_3$ of a dielectric object under test obtained from a minimum power reflection coefficient $R_m$ and a corresponding frequency $f_m$ measured in a structure in which a plane parallel plate manufactured according to the conditions of Equations 5 and 6 in the free space is inserted into an front end of the dielectric object as shown in FIG. 1 is calculated as in Equations 7 and 8:

$$n_3 = P + \sqrt{P^2 - Q} \qquad (7)$$

$$\text{wherein, } P = \frac{(1+B^2)(1-C^2)n_2}{(1-C)^2 + B^2(1+C)^2},$$

$$Q = \frac{(1+B^2)(1-C^2)^2 n_2^2}{(1-C)^2 + B^2(1+C)^2},$$

$$B = \tan\left[(2s+1)\pi - \frac{4\pi n_2 h_2 f_m}{c}\right], \text{ and}$$

$$C = \left[\frac{r_{12} + \sqrt{R_m}}{1 + r_{12}\sqrt{R_m}}\right]^2 \exp\left(\frac{8\pi f_m k_2 h_2}{c}\right).$$

A sign "±" is determined depending on a relative difference between magnitudes $r_{12}$ and $r_{23}$ of two basic reflection coefficients.

$$k_3 = \sqrt{\frac{r_{23}^2(n_2+n_3)^2 - (n_2-n_3)^2}{1 - r_{23}^2}} \qquad (8)$$

The complex permittivity of the dielectric object is determined by a relation between a complex refractive index and a complex permittivity as in Equation 9:

$$\epsilon' = n^2 - k^2; \quad \epsilon'' = 2nk \qquad (9)$$

Figure 2:
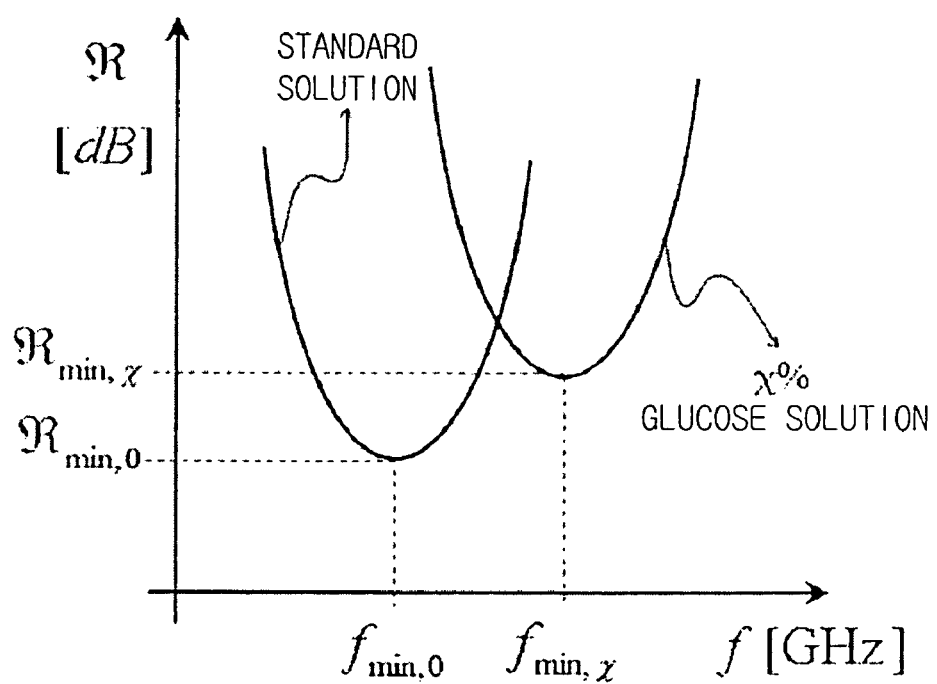
FIG. 2 is a graph expressing power reflection coefficients of a reference solution not including glucose and a ?% glucose solution as a function of frequency using the measurement principle of the device for the non-invasive measurement of blood glucose concentrations using millimeter waves according to an exemplary embodiment of the present invention.

FIG. 2 is a graph expressing power reflection coefficients of a reference solution not including glucose and a ?% glucose solution as a function of frequency using the measurement principle of the device for the non-invasive measurement of the blood glucose concentration using millimeter waves according to an exemplary embodiment of the present invention. When the reference solution changes the ?% glucose solution by adding glucose into the reference solution, the minimum power reflection coefficient and the corresponding frequency respectively shift from $R_{min,0}$ and $f_{min,0}$ to $R_{min,x}$ and $f_{min,x}$. As a result, a complex permittivity of ?% glucose solution may be determined using Equations 7 and 8. Also, a correlation between a glucose concentration and measurement parameters may be obtained. In addition, a glucose concentration of an unknown solution may be determined from such a correlation using measurement parameters.

Figure 3:
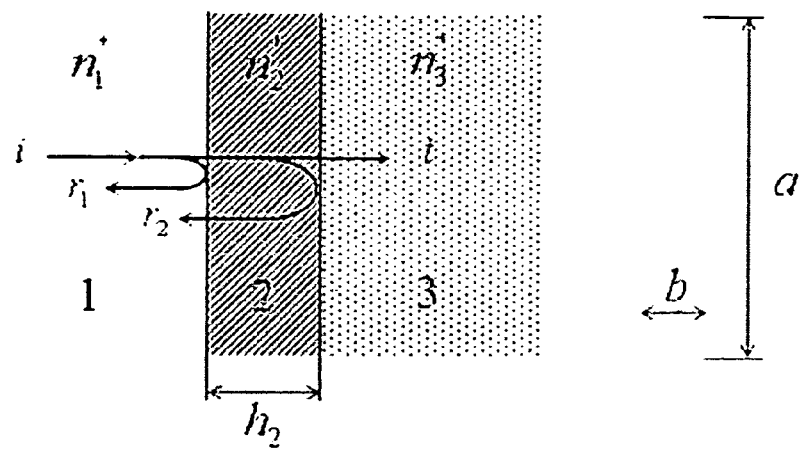
FIG. 3 is a view illustrating a plane parallel plate inserted into a TE10 mode waveguide according to an exemplary embodiment of the present invention.

The plane parallel plate may be inserted between the TE10 mode waveguide and the object under test to determine its dielectric characteristic and glucose concentration. FIG. 3 is a view illustrating a structure in which the plane parallel plate is inserted into the TE10 mode waveguide. In a case where the plane parallel plate is inserted into the TE10 mode waveguide having a×b (a>>b) rectangular shape as shown in FIG. 3, the propagating wavenumbers of millimeter waves propagated through media 1, 2, and 3 are given as in Equation 10:

$$\beta_j^* = \frac{2\pi}{\lambda_0}\sqrt{(n_j^*)^2 - \left(\frac{\lambda_0}{\lambda_c}\right)^2} \qquad (10)$$

wherein j is 1, 2 or 3, $?_c$ denotes a cutoff wavelength which is 2×a in the TE10 mode waveguide as shown in FIG. 3.

When Equation 3 is compared with Equation 10, an effective complex refractive index n*gj in the TE10 mode waveguide corresponding to complex refractive indexes n*j in the free space can be defined as in Equation 11. As a result, all of the above-described equations for the uniform plane wave in the free space may be equally applied to obtain parameters necessary for measurement.

$$n_{gj}^* = \sqrt{(n_j^*)^2 - \left(\frac{\lambda_0}{\lambda_c}\right)^2} = n_{gj} + ik_{gj} \qquad (11)$$

In particular, since an effective refractive index $n_{g1}$ of the air is not 1, the effective refractive index $n_{g2}$ of the plane parallel plate is given as in Equation 12:

$$n_{g2} = \sqrt{n_{g3}n_{g1} + \frac{n_{g1}k_{g3}^2}{n_{g3} - n_{g1}}} \qquad (12)$$

Accordingly, in the case of the TE10 mode waveguide, the dielectric characteristic of the dielectric object may be determined from the minimum power reflection coefficient and the corresponding frequency, measured using Equations applied to the case where a uniform plane wave is incident in free space together with Equations 11 and 12, and a temperature of the object.

Two types of measuring devices may be embodied based on the above-described measuring method. First, there may be embodied a measuring device in which a plane parallel plate having a refractive index $n_2$ and a thickness $h_2$ determined by Equations 12 and 6 according to a measuring frequency band is inserted into the TE10 mode waveguide. This is called a method of dielectric insertion (MDI). Also, there may be a measuring device in which a horn antenna is installed at the end of the TE10 mode waveguide and a plane parallel plate having the refractive index $n_2$ and the thickness $h_2$ determined by Equations 5 and 6 according to the measuring frequency band or a quasi-optical cuvette including the plane parallel plate is disposed at a front end of the dielectric object so as to measure the dielectric characteristic of the object under test in free space. This is called a method of auxiliary plate (MAP).

Figure 4:
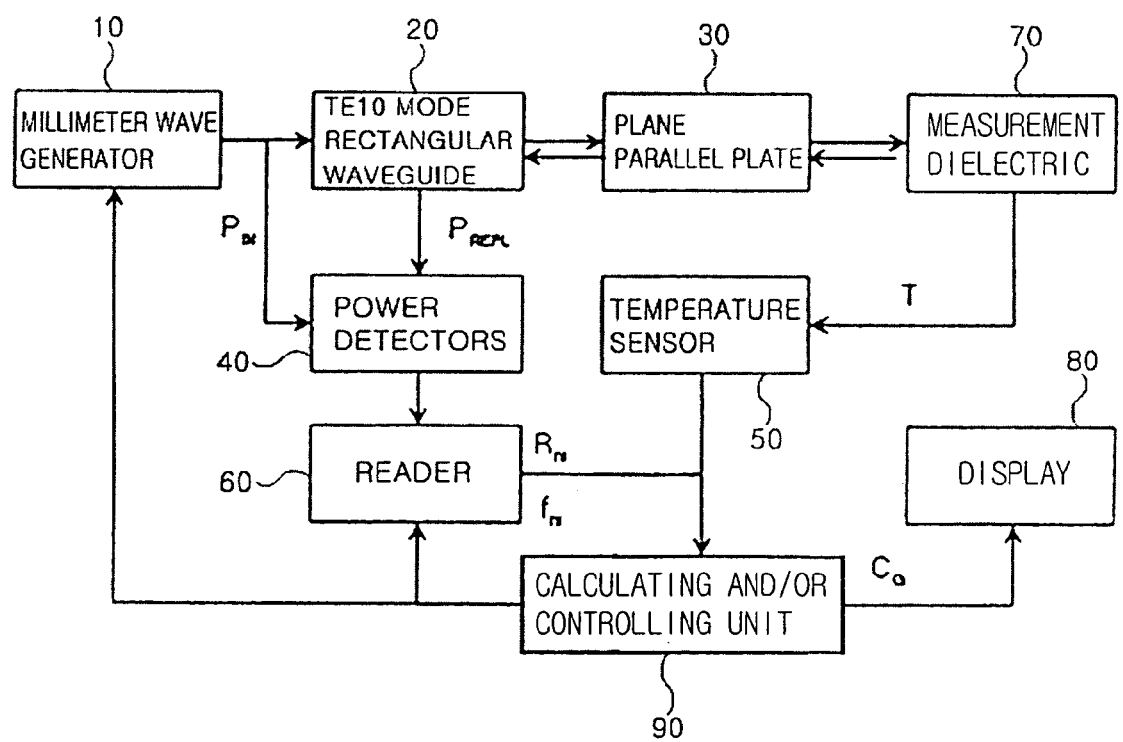
FIG. 4 is a block diagram of a device for a non-invasive measurement of blood glucose concentrations according to an exemplary embodiment of the present invention.
Figure 5:
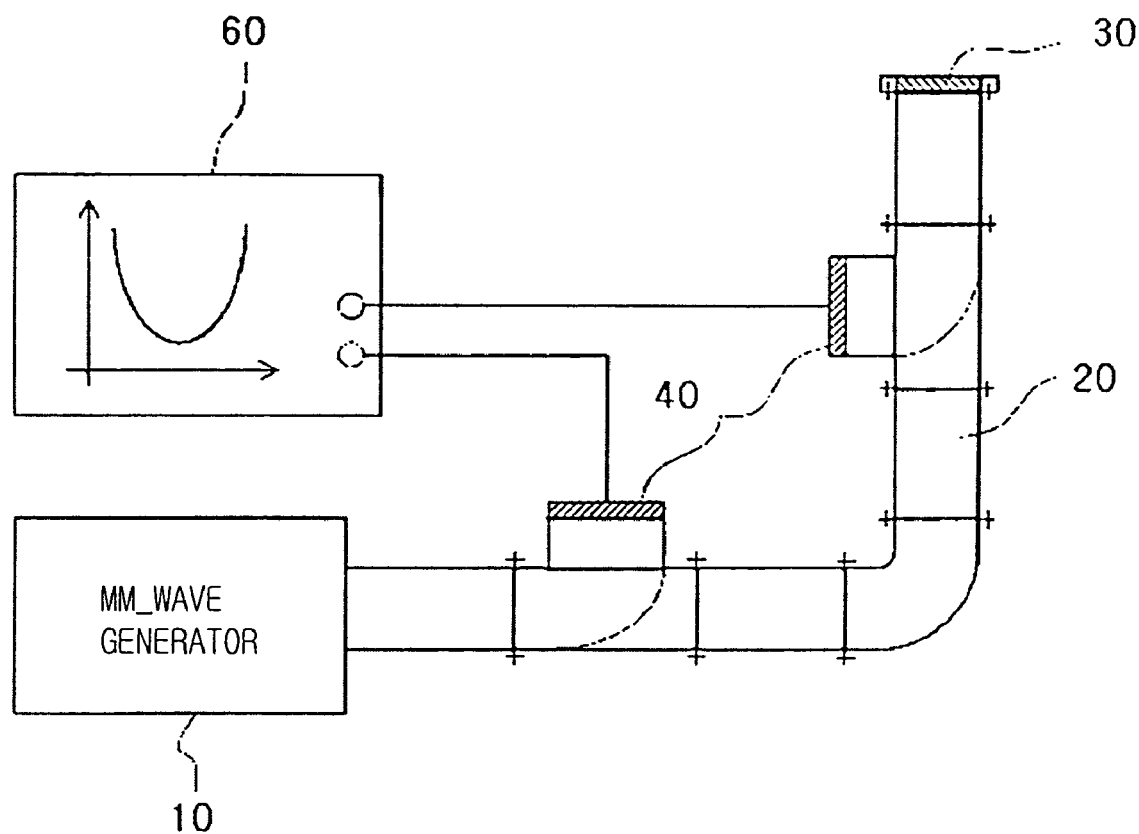
FIG. 5 is a schematic view of a device for a non-invasive measurement of blood glucose concentrations using millimeter waves according to an exemplary embodiment of the present invention.

FIGS. 4 and 5 are a block diagram and a schematic view of a device for a non-invasive measurement of blood glucose concentrations according to an exemplary embodiment of the present invention. The device includes a millimeter wave generator 10, a TE10 mode rectangular waveguide 20, a plane parallel plate 30, power detectors 40, a temperature sensor 50, and a reader 60. The device may further include a display 80, and a calculating and/or controlling unit 90.

The millimeter wave generator 10 generates an electromagnetic wave in a specified frequency band and may include a semiconductor resonator such as a backward wave oscillator (BWO) or a Gunn Diode.

The TE10 mode rectangular waveguide 20 transmits a millimeter wave, generated by the millimeter wave generator 10, to the plane parallel plate 30 and the dielectric object 70 under test. The TE10 mode rectangular waveguide 20 may composed of several components such as waveguide directional couplers, sections, and bends depending on the arrangement of the other elements.

The plane parallel plate 30 is formed of a material such as ceramic, fiber-glass, crystal quartz, fused quartz, or the like having a low dielectric loss with a refractive index and thickness chosen to yield a minimal point of the power reflection coefficient of the reflected millimeter wave in the specified frequency band. The plane parallel plate 30 is also installed at the end of the TE10 mode rectangular waveguide 20 so as to be positioned at the front end of the dielectric object. In the case of the MDI, the plane parallel plate 30 is inserted into the end of the TE10 mode rectangular waveguide 20. In the case of the MAP, the horn antenna is installed at the end of the TE10 mode rectangular waveguide 20, and the plane parallel plate 30 or the quasi-optical cuvette including the plane parallel plate 30 is between the end of the horn antenna and the front end of the dielectric object.

Plane parallel plates and quasi-optical cuvettes were manufactured as shown in Table 1 below to inspect variations in dielectric characteristics of a glucose solution, a glucose-saline (0.9% NaCl) solution, blood, and the skin of the body with respect to their glucose concentrations in the frequency band between 10 GHz and 150 GHz. Plane parallel plates to be used in the MDI are written in Table 1 to be applied in a frequency range between 10 GHz and 80 GHz, and plane parallel plates of quasi-optical cuvettes are also written for the measurement in the frequency band between 80 GHz and 100 GHz according to the MAP. A refractive index $n_2$ and a thickness $h_2$ of each plane parallel plate were determined as in Equations 5, 6, 11, and 12 using a dielectric constant $e'_2$ and a dielectric loss $e''_2$ of a pure water, as a reference solution for the glucose solutions, given in a function of a frequency and a temperature known by J. Liebo et al. The refractive index $n_2$ and the thickness $h_2$ of the plane parallel plate may be determined from the known dielectric characteristics of the body skin or blood to measure blood glucose concentrations in the body skin or blood samples.

TABLE 1

| Frequency Band | Refractive Index ($n_2$) | Absorption Rate ($k_2$) | Thickness ($h_2$), mm | Long Width (a), mm | Short Width (b), mm |
|---|---|---|---|---|---|
| 9~10 | 2.58 | 0.05 | 3.08 | 23 | 10 |
| 28~29 | 2.46 | 0.038 | 3.26 | 7.2 | 3.4 |
| 31~32 | 2.46 | 0.002 | 2.91 | 7.2 | 3.4 |
| 36~37 | 2.46 | 0.013 | 2.43 | 7.2 | 3.4 |
| 42~43 | 1.99 | 0.035 | 2.72 | 5.2 | 2.6 |
| 47~48 | 2.927 | 0.065 | 3.75 | 5.2 | 2.6 |
| 58~59 | 2.332 | 0.065 | 3.81 | 5.2 | 2.6 |
| 62~65 | 2.182 | 0.01 | 2.80 | 3.6 | 1.8 |
| 77~78 | 2.294 | 0.06 | 3.82 | 3.6 | 1.2 |
| 83~84 | 2.17 | 0.01 | 2.00 | 14 | 14 |
| 92~93 | 2.11 | 0.005 | 1.83 | 14 | 14 |
| 99~100 | 2.11 | 0.005 | 3.95 | 14 | 14 |
| 102~103 | 2.13 | 0.017 | 3.62 | 20 | 20 |

The power detectors 40 are attached to ends of two directional couplers of the TE10 mode rectangular waveguide 20 and detect a power $P_{IN}$ of an incident wave generated by the millimeter wave generator 10 and a power $P_{REFL}$ of a reflected wave from the object through the plane parallel plate 30.

The temperature sensor 50 contacts the object parallel to the plane parallel plate 30 and measures its temperature to compensate fro the variations of the measured power reflection coefficient and frequency caused by the temperature changes of the object.

The reader 60 reads the minimum power reflection coefficient and the corresponding frequency from the power $P_{IN}$ of the incident wave and the power $P_{REFL}$ of the reflection wave detected by the power detectors 40. The reader 60 may include an SWR and/or attenuation meter, a digital indicator, an oscilloscope, and the like.

In the device for the non-invasive measurement of blood glucose concentrations, the power detectors 40 detect the incident wave, having a specified frequency band, generated by the millimeter wave generator 10 and the reflected wave from the dielectric object through the waveguide 20 and the plane parallel plate 30. The reader 60 then reads the minimum power reflection coefficient and the corresponding frequency in the specified frequency band and displays a resultant wave as shown in FIG. 2. As a result, the glucose concentration of the object under test is determined from a correlation among the glucose concentration of the object and the measured parameters, i.e., the minimum power reflection coefficient, the corresponding frequency, and the temperature.

In particular, when blood glucose level is non-invasively measured from the skin of the body, an individual difference may occur between users. Also, the measured parameters may be affected by different test conditions as well as the temperature of the human body. Thus, a calculating unit may further include an algorithm for compensating for the individual difference and the influences of test conditions. In addition, a controller and a display may be included to automatically measure and display the blood glucose level of the human body.

To confirm the measurement method of the device for the non-invasive measurement of blood glucose concentrations according to the present invention, the complex permittivity of 18° C. pure water was measured in frequency bands between 9 GHz and 10 GHz, 42 GHz and 43 GHz, and 50 GHz and 65 GHz. Next, the complex permittivities of a glucose-water solution and a glucose-saline (0.9% NaCl) solution with respect to each glucose concentration were measured in the frequency bands between 9 GHz and 10 GHz, 42 GHz and 43 GHz, and 50 GHz and 65 GHz.

Table 2 below shows the dielectric constants and losses of 18° C. pure water, measured in the frequency bands between 9 GHz and 10 GHz, 42 GHz and 43 GHz, and 50 GHz and 65 GHz, in comparison with calculated values, according to the well-known spectral model for the complex permittivity of pure water suggested by J. Liebe et al. (J. Liebe. A. G. A. Hufford and T. Manabe, "A model for the complex permittivity of water at frequencies below 1 THz," Int. J. of infrared and Millimeter Waves, Vol. 12, No. 7, pp. 659-675, 1991.).

TABLE 2

| Frequency [GHz] | Dielectric Constant ($e'_w$) | | | Dielectric Loss ($e''_w$) | | |
|---|---|---|---|---|---|---|
| | Measured Value (A) | Experienced Value (B) | \|A − B\|/B | Measured Value (C) | Experienced Value (D) | \|C − D\|/D |
| 9.318 | 62.22 | 61.78 | 0.7% | 33.30 | 32.77 | 0.1% |
| 42.81 | 14.80 | 14.69 | 0.7% | 24.95 | 24.91 | 0.2% |
| 62.32 | 10.12 | 10.09 | 0.3% | 18.37 | 18.40 | 0.2% |

Table 2 shows the experienced values obtained according to the spectral model for the complex permittivity of pure water, which had been well established based on numerous experimental data in various frequency ranges by many researchers. Also, as shown, the measured values according to the present invention have differences below 1% from the experienced ones according to the spectral model.

To measure the dielectric characteristic of the glucose solution, matching plates corresponding to the frequency bands between 9 GHz and 10 GHz, 42 GHz and 43 GHz, and 50 GHz and 65 GHz are inserted into the TE10 mode rectangular waveguide to use a glucose solution having a glucose concentration between 0 wt. % and 5 wt. %. Table 3 below shows the minimum power reflection coefficient $R_m$ and the corresponding frequency $f_m$ measured with respect to each glucose concentration.

TABLE 3

| | 9-10 GHz | | 42-43 GHz | | 60-65 GHz | |
|---|---|---|---|---|---|---|
| x[wt %] | $R_m$[dB] | $f_m$[GHz] | $R_m$[dB] | $f_m$[GHz] | $R_m$[dB] | $f_m$[GHz] |
| 0 | 27.3 | 9.318 | 24.6 | 42.81 | 24.8 | 62.32 |
| 2 | 26.2 | 9.309 | 25.7 | 42.80 | 23.6 | 62.30 |
| 3 | 25.7 | 9.303 | 26.0 | 42.78 | 23.0 | 62.29 |
| 4 | 25.2 | 9.298 | 26.6 | 42.77 | 22.6 | 62.28 |
| 5 | 24.8 | 9.290 | 27.4 | 42.76 | 22.4 | 62.27 |

Figure 6:
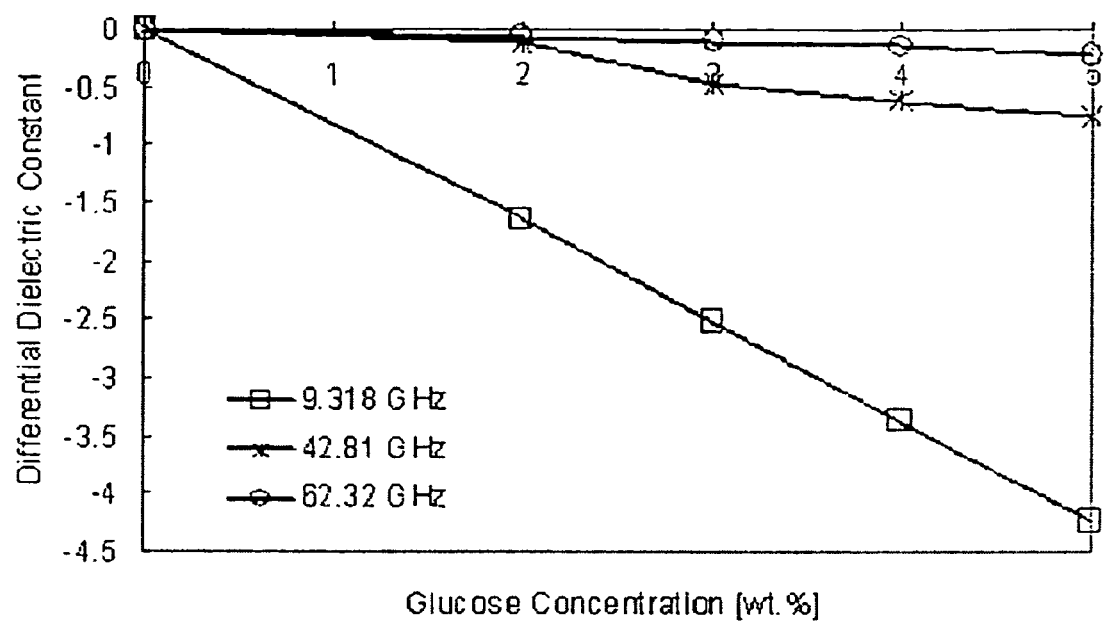
FIGS. 6 and 7 are graphs illustrating a differential dielectric constant ?e'x and a differential dielectric loss ?e''x of a glucose solution with respect to its glucose concentration at each measuring frequency using a device for a non-invasive measurement of blood glucose concentrations using millimeter waves according to an exemplary embodiment of the present invention.
Figure 7:
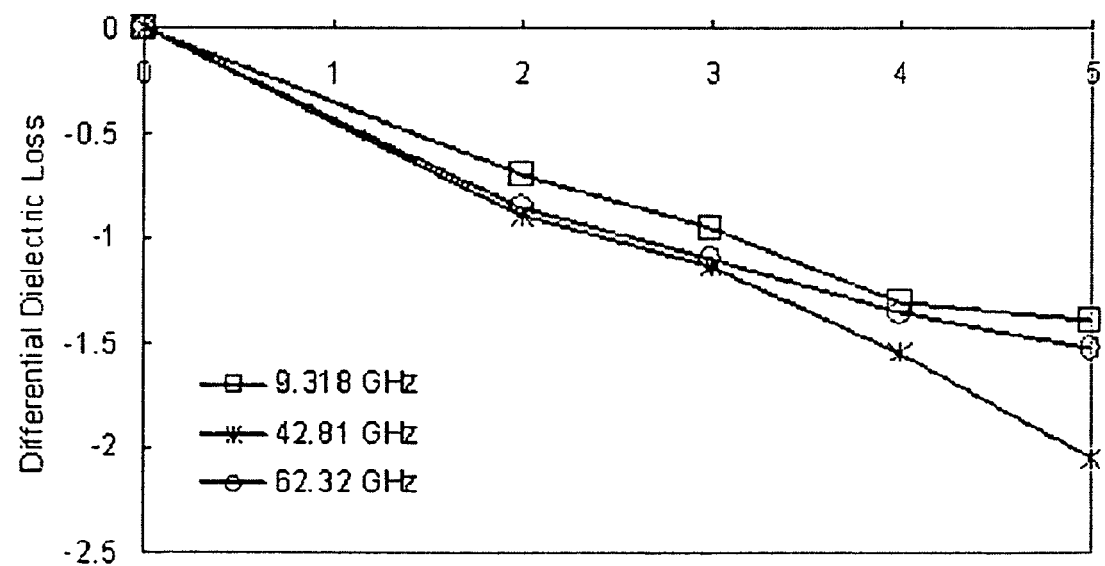

The dielectric constant $e'_x$ and dielectric loss $e''_x$ of the glucose-water solution were obtained from the measurement results shown in Table 3 according to the above-described dielectric characteristic calculation method. FIGS. 6 and 7 are graphs showing a differential dielectric constant ?$e'x$ and a differential dielectric loss ?$e''_x$ of the pure water and the glucose-water solution with respect to the glucose concentration at each frequency.

According to the measurement results of a 25° C. glucose solution having a molar fraction between 0.01 and 0.04 at an existing frequency of 10 GHz (A. Saito, O. Miyawaki, and K. Nakamura, "Dielectric Relaxation of Aqueous Solution with Low-molecular-weight Nonelectrolytes and Its Relationship with Solution Structure", Biosci. Biotech. Biochem., Vol. 61, No. 11, pp. 1831-1835, 1997.), the dielectric constant of a glucose solution having a molar fraction of 0.01 (9.2 wt %) shows a difference of about −7 from the dielectric constant of the pure solution. Also, a dielectric constant of a glucose solution having a molar fraction of 0.04 (29.4 wt %) shows a difference of about −30. Thus, a ratio of the dielectric constant to the glucose concentration is about −1.1 ?e'?/wt. %. A ratio of the dielectric constant to the glucose concentration is −0.8 ?e'?/wt. % at a temperature of 18° C. Considering the difference in the measured temperature, the results of the existing experiment are similar to the results of the experiment of the present invention.

Table 4 below shows the minimum power reflection coefficient and the corresponding frequency of the saline (0.9% NaCl) solution and a glucose-0.9% NaCl solution made by adding glucose between 0.4 wt. % and 0.5 wt. % to the saline at a temperature of 17° C. in a frequency band of 83 GHz.

TABLE 4

| ?[wt %] | $R_m$[dB] | $f_m$[GHz] |
|---|---|---|
| 0.0 | 24.4 | 83.02 |
| 0.4 | 23.7 | 83.02 |
| 0.5 | 23.3 | 83.02 |

As shown in Table 4, the minimum power reflection coefficient varies by 0.5 dB with a variation in the glucose concentration of 1.0 wt. % according to the measurement result using the plane parallel plate. In a case where the resolutions in the measurement of the power reflection coefficient and the frequency are respectively 0.1 dB and 0.01 Ghz, about 0.05 wt. % (about 3 mmol/L) difference in the glucose concentration of the glucose-saline (0.9% NaCl) solution could be discriminated.

In the device for the non-invasive measurement of blood glucose concentrations according to the present invention, a substantial refractive index of a plane parallel plate affects the measurement accuracy of the device and the sensitivity to the glucose concentrations of the object under test. Thus, the plane parallel plate may be developed to reduce a power reflection coefficient to less than −35 dB in order to enhance the measurement accuracy of the device.

Accordingly, the results of the experiment with respect to the 18° C. glucose solution in the frequency bands between 9 GHz and 10 GHz, 42 GHz and 43 GHz, and 50 GHz and 65 GHz show the potential of the measurement method of the present invention. According to the experiment of the 17° C. glucose-0.9% NaCl solution in a frequency band between 80 GHz and 85 GHz according to the method of the present invention, about 3 mmol/L variations of the glucose concentration in the solution could be discriminated with the resolutions of 0.1 dB and 0.01 GHz respectively.

As described above, in a device for the non-invasive measurement of blood glucose concentrations by millimeter waves and a method thereof according to the present invention, a plane parallel plate having a low dielectric loss determined according to the measuring frequency band can be disposed at a front end of a dielectric object under test to form minimum reflection conditions. Thus, a minimum power reflection coefficient and a corresponding frequency can be measured to determine a dielectric characteristic of the dielectric object. As a result, non-invasive or invasive measurement using millimeter waves can be achieved.

Also, a compact blood glucose measuring device enough to be mounted in a portable device such as a cellular phone or the like can be manufactured.

In addition, periodic self-monitoring of blood glucose can be smoothly performed according to the non-invasive measurement method to help the management of diabetes of diabetics.

Moreover, additional cost is not required for diagnostic strips, diagnostic reagents, or the like. Thus, the economic burden of patients and the family of the patients can be reduced.

The foregoing embodiments and advantages are merely exemplary and are not to be construed as limiting the present invention. The present teaching can be readily applied to other types of apparatuses. Also, the description of the embodiments of the present invention is intended to be illustrative, and not to limit the scope of the claims, and many alternatives, modifications, and variations will be apparent to those skilled in the art.

What is claimed is:

1. A device for a non-invasive measurement of blood glucose concentrations by millimeter waves, the device comprising:
    a millimeter wave generator which creates an electromagnetic wave in a specified frequency band;
    a TE10 mode rectangular waveguide which transmits a millimeter wave generated by the millimeter wave generator;
    a plane parallel plate which has a refractive index and a thickness determined to yield a minimal power reflection coefficient of the electromagnetic wave in the specified frequency band and which is installed at an end of the TE10 mode rectangular waveguide to be positioned at a front end of a dielectric object under test;
    power detectors which detect the powers of an incident wave generated by the millimeter wave generator and a reflected wave from the dielectric object through the plane parallel plate;
    a temperature sensor which measures a temperature of the dielectric object; and
    a reader which reads the minimum power reflection coefficient and a corresponding frequency of the reflected wave from the powers of the incident and reflected waves detected by the power detectors.

2. The device of claim 1, wherein the refractive index of the plane parallel plate is defined by the following equation:

$$n_2 = \sqrt{n_3 + \frac{k_3^2}{n_3 - 1}}$$

wherein $n_2$ denotes the refractive index of the plane parallel plate, $n_3$ denotes an approximate refractive index of the dielectric object, and $k_3$ denotes an approximate absorption rate of the dielectric object.

3. The device of claim 1, wherein the thickness of the plane parallel plate is defined by the following equation:

$$h_2 = \frac{(2s+1)c}{4n_2 f_m} - \arctan\left(\frac{2n_2 k_3}{n_3^2 + k_3^2 - n_2^2}\right)\frac{c}{4\pi n_2 f_m}$$

wherein $h_2$ denotes the thickness of the plane parallel plate, $s$ denotes an arbitrary integer, $c$ denotes a speed of light in a free space, $n_2$ denotes the refractive index of the plane parallel plate, $f_m$ denotes a frequency in which a minimum reflection condition occurs, and $k_3$ denotes an approximate absorption rate of the dielectric object.

4. The device of claim 1, wherein a complex refractive index $n_3 + ik_3$ of the dielectric object obtained from the minimum power reflection coefficient and the corresponding frequency measured by the reader is defined by the following equation:

$$n_3 = P + \sqrt{P^2 - Q}$$

$$k_3 = \sqrt{\frac{r_{23}^2(n_2+n_3)^2 - (n_2-n_3)^2}{1 - r_{23}^2}}$$

wherein $n_2$ denotes the refractive index of the plane parallel plate, $n_3$ denotes the refractive index of the dielectric object, $k_3$ denotes the absorption rate of the dielectric object, $r_{23}$ denotes a reflection coefficient at an interface between the plane parallel plate and the dielectric object, $$P = \frac{(1+B^2)(1-C^2)n_2}{(1-C)^2 + B^2(1+C)^2},$$

$$Q = \frac{(1+B^2)(1-C^2)^2 n_2^2}{(1-C)^2 + B^2(1+C)^2},$$

$$B = \tan\left[(2s+1)\pi - \frac{4\pi n_2 h_2 f_m}{c}\right], \text{ and}$$

$$C = \left[\frac{r_{12} + \sqrt{R_m}}{1 + r_{12}\sqrt{R_m}}\right]^2 \exp\left(\frac{8\pi f_m k_2 h_2}{c}\right).$$

5. A non-invasive measurement method of a blood glucose concentration by millimeter waves, the method comprising:
    installing a plane parallel plate, of which a refractive index and thickness are chosen to yield a minimal point of a power reflection coefficient in a specified frequency band, at an end of a TE10 mode rectangular waveguide transmitting a millimeter wave to be positioned at a front end of a dielectric object under test;
    detecting the minimum power reflection coefficient and a corresponding frequency of the millimeter wave incident to and reflected from the dielectric object under test via the TE10 mode rectangular waveguide and the plane parallel plate;
    measuring a temperature of the dielectric object; and
    determinating a glucose concentration of the dielectric object from the minimum power reflection coefficient, the corresponding frequency, and the temperature of the dielectric object.

6. The non-invasive measurement method of claim 5, wherein the refractive index of the plane parallel plate is defined by the following equation:

$$n_2 = \sqrt{n_3 + \frac{k_3^2}{n_3 - 1}}$$

wherein $n_2$ denotes the refractive index of the plane parallel plate, $n_3$ denotes an approximate refractive 7. The non-invasive measurement method of claim 5, wherein the thickness of the plane parallel plate is defined by the following equation:

$$h_2 = \frac{(2s+1)c}{4n_2 f_m} - \arctan\left(\frac{2n_2 k_3}{n_3^2 + k_3^2 - n_2^2}\right)\frac{c}{4\pi n_2 f_m}$$

wherein $h_2$ denotes the thickness of the plane parallel plate, s denotes an arbitrary integer, c denotes a speed of light in a free space, $n_2$ denotes the refractive index of the plane parallel plate, $f_m$ denotes a frequency in which a minimum reflection condition occurs, and $k_3$ denotes an approximate absorption rate of the dielectric object.

8. The non-invasive measurement method of claim 5, wherein a complex refractive index $n_3+ik_3$ of the dielectric object obtained from the minimum power reflection coefficient and the corresponding frequency measured by the reader is calculated by the following equation:

$$n_3 = P + \sqrt{P^2 - Q}$$

-continued $$k_3 = \sqrt{\frac{r_{23}^2(n_2+n_3)^2 - (n_2-n_3)^2}{1 - r_{23}^2}}$$

wherein $n_2$ denotes the refractive index of the plane parallel plate, $n_3$ denotes the refractive index of the dielectric object (the real part of the complex refractive index), $k_3$ denotes the absorption rate of the dielectric object, $r_{23}$ denotes a reflection coefficient at an interface between the plane parallel plate and the dielectric object, $$P = \frac{(1+B^2)(1-C^2)n_2}{(1-C)^2 + B^2(1+C)^2},$$

$$Q = \frac{(1+B^2)(1-C^2)^2 n_2^2}{(1-C)^2 + B^2(1+C)^2},$$

$$B = \tan\left[(2s+1)\pi - \frac{4\pi n_2 h_2 f_m}{c}\right], \text{ and}$$

$$C = \left[\frac{r_{12} + \sqrt{R_m}}{1 + r_{12}\sqrt{R_m}}\right]^2 \exp\left(\frac{8\pi f_m k_2 h_2}{c}\right).$$

\* \* \* \* \*